(12) United States Patent
Brånemark

(10) Patent No.: US 7,753,942 B2
(45) Date of Patent: Jul. 13, 2010

(54) FIXTURE

(75) Inventor: Per-Ingvar Brånemark, Mölndal (SE)

(73) Assignee: Medevelop AB, Gothenburg (SE)

( * ) Notice: Subject to any disclaimer, the term of this patent is extended or adjusted under 35 U.S.C. 154(b) by 0 days.

(21) Appl. No.: 10/540,089

(22) PCT Filed: Dec. 18, 2003

(86) PCT No.: PCT/SE03/02015

§ 371 (c)(1),
(2), (4) Date: Jun. 20, 2005

(87) PCT Pub. No.: WO2004/056285

PCT Pub. Date: Jul. 8, 2004

(65) Prior Publication Data

US 2006/0173460 A1    Aug. 3, 2006

(30) Foreign Application Priority Data

Dec. 19, 2002   (SE) ..................... 0203786

(51) Int. Cl.
*A61B 17/58* (2006.01)
(52) U.S. Cl. ..................... 606/301
(58) Field of Classification Search .............. 606/60, 606/62, 64, 72, 73; 411/386
See application file for complete search history.

(56) References Cited

U.S. PATENT DOCUMENTS

| 1,708,793 | A | * | 4/1929 | Jones ..................... 384/396 |
| 2,113,600 | A | * | 4/1938 | Olson ..................... 411/386 |
| 2,232,336 | A | * | 2/1941 | Meersteiner ............. 411/421 |
| 3,022,701 | A | * | 2/1962 | Potruch ................. 411/80.1 |
| 3,979,829 | A | * | 9/1976 | Lemos .................... 433/165 |
| 4,697,969 | A | * | 10/1987 | Sparkes ................. 411/387.7 |
| 5,171,284 | A | * | 12/1992 | Branemark ............... 606/63 |
| 5,334,204 | A | * | 8/1994 | Clewett et al. ........... 606/73 |
| 5,489,210 | A | * | 2/1996 | Hanosh .................. 433/173 |
| 5,702,445 | A | * | 12/1997 | Brånemark ............... 606/60 |
| 5,725,581 | A | * | 3/1998 | Brånemark ............... 606/73 |
| 5,727,943 | A |   | 3/1998 | Beaty et al. |
| 5,759,003 | A | * | 6/1998 | Greenway et al. ......... 411/421 |
| 5,769,852 | A | * | 6/1998 | Brånemark ............... 606/65 |
| 5,871,356 | A | * | 2/1999 | Guedj ................... 433/174 |
| 6,290,701 | B1 | * | 9/2001 | Enayati .................. 606/72 |
| 6,402,757 | B1 | * | 6/2002 | Moore et al. ............. 606/80 |
| 7,017,952 | B2 | * | 3/2006 | Brewer et al. ............ 285/391 |

FOREIGN PATENT DOCUMENTS

| EP | 1 145 691 A1 | 10/2001 |
| WO | WO 9701306 A1 * | 1/1997 |
| WO | WO 9703621 A1 * | 2/1997 |

* cited by examiner

*Primary Examiner*—Thomas C Barrett
*Assistant Examiner*—Nicholas Woodall
(74) *Attorney, Agent, or Firm*—The Maxham Firm

(57) ABSTRACT

A fixture which is intended to be screwed firmly into bone tissue. The fixture includes a generally cylindrical anchoring portion provided with an external screw thread. The anchoring portion includes a cavity which extends from the insertion end of the anchoring portion. A number of slots which connect the cavity with the outside of the anchoring portion extend from the insertion end of the anchoring portion. Each slot is delimited by a leading slot wall and a trailing slot wall, the leading and trailing slot walls rotating in the direction defined by the screw thread when screwing in the anchoring portion. At least the radially outermost part of the trailing slot wall defines an angle with the radial direction and is inclined obliquely forward from within and outward in the direction of rotation.

24 Claims, 1 Drawing Sheet

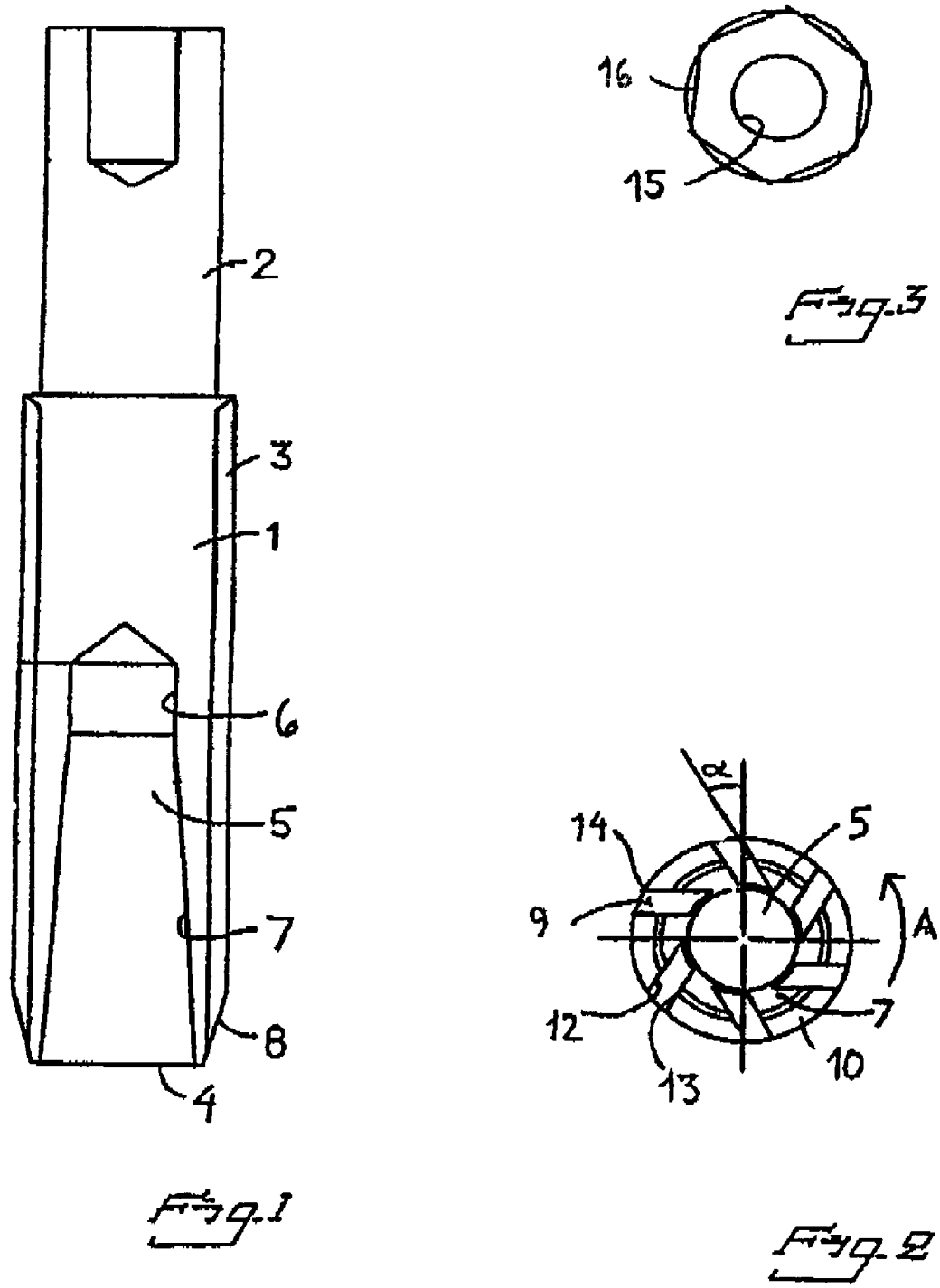

FIXTURE

FIELD OF THE INVENTION

The present invention relates to a so-called fixture which is intended to be screwed firmly into bone tissue and which is of the kind that includes a generally cylindrical anchoring portion that is provided with an external screw thread, which anchoring portion which has a cavity which opens out at the insertion end of the anchoring portion, and a number of through-penetrating slots which extend from said insertion end, wherein each slot connects the cavity with the outer side of the anchoring portion and wherein each slot is delimited by a leading and a trailing slot wall, where the leading and trailing walls relate to the direction of rotation defined by the screw thread when screwing in the fixture.

BACKGROUND OF THE INVENTION

Fixtures of this kind are used in the field of prosthetic surgery, wherein the prosthesis, parts of a prosthesis or a prosthesis holder is/are anchored in the bone tissue of a person with the aid of one or more such fixtures.

However, the fixtures according to the present invention are intended primarily to be anchored in hollow or tubular bone and can be used, for instance, in the reconstruction of joints, for instance finger joints or hip joints. The fixtures can also be used to fasten artificial legs or other types of prostheses. However, the invention is not limited to such applications. The fixture has an anchoring portion and an application portion. The anchoring portion is screwed into a hole pre-drilled in the bone tissue. The hole is given a diameter which is smaller than the outer diameter of the screw thread of the anchoring portion. The anchoring portion is self-tapping and thus produces a screw thread in the wall of the predrilled hole when screwed thereinto, while removing bone fragments. Screwing of the anchoring portion into said hole is facilitated by the slots, by virtue of the bone fragments being pulled loose from the hole by the edges formed between the outer periphery of the anchoring portion and the slots. These bone fragments are conveyed to said cavity through the slots.

An example of such a fixture is described in EP 0 595 782, in which the anchoring end of the fixture is provided with four helically extending slots. This known fixture has been found highly satisfactory in many respects and has provided reliable and positive anchorage of a prosthesis fastened with such a fixture.

However, the known fixture has certain drawbacks. For example, as the fixture is rotated, the bone tissue is worked by those edges that are formed between the periphery of the anchoring portion and the trailing walls of respective slots. The edge between the radially directed slot wall and said peripheral surface generally defines a right angle. Such an edge works the bone tissue primarily by rubbing against and tearing loose bone fragments from the wall of the predrilled hole when screwing in the anchoring portion. This results in an unfavourable harsh action on the bone tissue. Moreover, the bone fragments that are so loosened are unusually large and of an irregular shape. This makes recovery and healing of the bone material that collects in the cavity of said fixture difficult to achieve.

Another drawback with the known fixture is that the radial slots cause the geometry of the anchoring portion to become unfavourable when said portion is subjected to the compressive radially acting forces created when screwing the anchoring portion into the predrilled hole. The combined effect of the rotation of the anchoring portion and of the forces that act radially inwards cause the parts situated between the slots to become distorted as a result of said compression, therewith causing the fastening portion to be deformed to a non-round shape. This reduces the strength of the anchorage. Although this deformation can be avoided by increasing the wall thickness of said portions, this increase in wall thickness will cause the anchoring portion to become stiffer and make it difficult to achieve the radial elasticity desired to achieve a strong anchorage.

The object of the present invention is to provide an improved type of fixture in which the aforedescribed drawbacks are eliminated or at least reduced. The primary object of the invention is to provide a so-called fixture with which the bone fragments will be detached favourably when screwing in the fixture.

SUMMARY OF THE INVENTION

This object of the invention is achieved by virtue of the trailing slot wall in the anchoring portion defining an angle with the radial direction and sloping obliquely forwards from within and outwards in the direction in which the fixture is rotated as it is screwed in, said angle being defined at least at the radially outer part of the anchoring portion.

As a result of the trailing slot wall being so inclined, there is defined an acute angle between said wall and the periphery of the anchoring portion. As a result of this acute angle, working of the bone in the wall of the predrilled hole is achieved more effectively and more gently, such that bone fragments will be cut loose rather than being worn loose as in the case of earlier known fixtures of a corresponding kind. The acute angle thus provide a sharp edge that works in the manner of scalpel in detaching said bone fragments.

According to one preferred embodiment of the inventive fixture, it is not only the radially outermost part of said slot wall that defines said angle, but that the whole of the trailing slot wall defines the same angle. With regard to the actual working process, it will, per se, suffice for solely the outer parts to be inclined. By causing the whole of the slot wall to slope, there is also obtained a favourable geometry for the radial compression of the anchoring portion of the fixture as said anchoring portion is screwed in. When those parts of the anchoring portion located between the slots are pressed radially inwards, the obliquely extending trailing slot wall will support the leading slot wall, meaning that the anchoring portion will retain its circular shape even when radially compressed. The parts situated between the slots may be made relatively thin, so that the elasticity of said parts will facilitate radial compression of the anchoring portion. The possibility of compressing the anchoring portion radially while retaining its circular shape contributes further towards obtaining a strong and secure fastening.

According to another preferred embodiment, the leading slot wall slopes obliquely forwards from within and outwards in the direction in which the anchoring portion is rotated as it is screwed in. Because both slot walls are inclined, the geometrical conditions are improved still further, therewith contributing towards retaining the circular shape of the anchoring portion during the radial compression that occurs when screwing in said portion.

According to another preferred embodiment of the invention, the angle defined between the trailing slot wall and said radial direction is in the order of 20°-40°. In this angular range, the angle is sufficiently large to provide a good cutting action and sufficiently small to avoid the risk of fracture or like damage at the cutting edge. In the majority of applications, it is thought that an angle in the range of 27°-33° is most suitable, wherewith an angle of about 30° may be the most suitable.

According to another preferred embodiment, the number of slots ranges from 3 to 10, preferably from. 5 to 7, suitably six slots. The optimum number of slots may vary, primarily depending on the size of the fixture, in other words on the prosthesis application used. The optimum number of slots may also depend on other factors. In many instances, a fixture that includes about six slots constitutes the best balance between the aspects that must be observed in order to achieve favourable conditions for screwing in anchoring portion and also for achieving a secure and durable fastening.

According to another preferred embodiment, the cavity has a circular cross-sectional shape and widens conically in a direction towards the insertion end. As a result of this conical shape, those parts situated between the slots will have the form of tongues whose thicknesses decrease towards said insertion end. The flexibility of the tongues thus increases towards said insertion end so as to achieve the desired radial resilience or springiness of said tongues.

According to another preferred embodiment, the width of the slot at its radially outer end corresponds to 15-35% of the peripheral distance between two slots on the outside of the fixture. This relationship between slot width and slot spacing enables an optimum balance to be achieved between working-technical and strength-technical aspects of the function of the fixture.

According to a further preferred embodiment of the invention, the fixture is made of titanium. Although the fixture can be made of any other suitable material, for instance a polymeric material, composite material or other metals, it is preferred to use titanium. Titanium has mainly been found to possess the particular ability of adhering to bone material by so-called osseointegration in the absence of those negative reactions that often occur when foreign material is implanted in body tissue. On a molecular level, titanium is able to interact with and to integrate with bone tissue, such as to coalesce with the bone. This means that a titanium fixture will be anchored very securely.

These preferred embodiments of the inventive fixture will be apparent from the accompany dependent Claims.

The Invention also relates to the use of the inventive fixture in securing a prosthesis to bone tissue.

The inventive use provides advantages that correspond to those given above with respect to the inventive fixture and the preferred embodiments thereof.

The invention will be described in more detail below with reference to an advantageous embodiment of the inventive fixture and with reference to the accompanying drawings.

BRIEF DESCRIPTION OF THE DRAWINGS

FIG. 1 is a longitudinally sectioned view of a fixture according to the invention.

FIG. 2 is an end view of the fixture according to FIG. 1 as seen from the insertion end.

FIG. 3 is an end view seen from the application end of the fixture according to FIG. 1.

(The figures are drawn to a scale of 5:1).

DESCRIPTION OF ADVANTAGEOUS EMBODIMENTS

FIG. 1 is a longitudinal sectional view of an inventive fixture. The illustrated fixture is intended for a finger joint and is dimensioned to this end. The fixture comprises an anchoring portion 1 and an application portion 2. The anchoring portion has a length of about 20 mm and the application portion a length of about 10 mm.

The anchoring portion includes an external screw thread 3 which is adapted to allow the applicator to be screwed into a hole predrilled in the bone tissue. The thread is an M6 thread in the illustrated case. The predrilled hole will preferably have a diameter that is slightly smaller than the inner diameter of the thread, i.e. about 4.5 mm. The thread 3 extends along the full length of the anchoring portion 2.

The anchoring portion includes a cavity 5 that extends axially and centrally in the anchoring portion from the insertion end 4 thereof. The cavity has a depth of about 12 mm and includes farthest in a short cylindrical part 6 and a conical part 7 that is situated between said cylindrical part and said insertion end. The conical part has a length of about 10 mm, a smallest diameter of about 3 mm and a largest diameter of about 4.4 mm, corresponding to a cone angle of 40.

The anchoring portion 1 has at its insertion end 4 a beveling 8 which facilitates screwing of the anchoring portion 1 into the predrilled hole. The bevelling extends along about 2 mm of the fixture and has an angle of about 15°.

As before mentioned, FIG. 2 is an end view of the fixture as seen from its insertion end. As will be seen from FIG. 2, six slots 9 are disposed around the anchoring portion 1 of the fixture. Each slot connects the cavity 5 with the outer surface of the anchoring portion 1 and extends axially upwards along the major part of the cavity 5 from the insertion end. This therewith results in the formation of tongues 10 between the slots, where each tongue 10 decreases in thickness in a direction towards the insertion end 4.

Each slot is defined by two mutually parallel slot walls, that is to say a leading slot wall 13 and a trailing slot wall 12 as seen in the direction of rotation A when screwing in the anchoring portion. Each slot slopes forwards and outwards in said rotation direction. The slot walls 12, 13 thus define an angle $\alpha$ with the radial direction, said angle $\alpha$ being measured with respect to the intersection of respective slot walls with the outer surface of the anchoring portion. The angle $\alpha$ is about 30° in the illustrated case.

A sharp edge 14 is thus formed between the trailing slot wall 12 and the outer portion of the anchoring portion, said edge constituting a cutting edge when screwing in the anchoring portion. The cutting edge has a top angle of about 60°. Each slot has a width of about 0.5 mm, ie.e, the distance between the slot walls is about 0.5 mm.

FIG. 3 is an end view of the fixture as seen from the application end. The application end may be designed in different ways. In the case of the illustrated embodiment, the application end includes a central bore 15 having a diameter of 2.5 mm. The upper part of the application end has an hexagonal shape 16 to which a tool can be applied when screwing in the anchoring portion.

The illustrated fixture is secured in the manner described below.

Firstly, a hole is drilled in the bone tissue to which the fixture shall be fastened. The diameter of the hole drilled will be smaller than the inner diameter of the screw thread on the anchoring portion 1.

The fixture is then entered into the predrilled hole, facilitated by the bevelling 8 at the inner end 4 of the anchoring portion, and the fixture is turned in the direction of arrow A with the aid of a turning tool applied to the hexagonal shape 16. The fixture is then screwed into the hole, therewith tapping a screw thread therein. This is achieved with the aid of the slots 9, more specifically by the cutting edges 14 of respective trailing slot walls 12.

The sharp cutting edge 14 cuts loose chippings from the bone material in the wall of the predrilled hole, these chippings being transported through the slot 9 and collected in the cavity 5 within the anchoring portion of the fixture. At the same time, the tongues 10 formed between the slots 9 are pressed radially inwards by the pressure exerted from the defining wall of the predrilled hole, whereafter respective slot walls are pressed closer together so as to reduce the width of the slots. The obliqueness of the slots results in a supportive action therebetween. This obliqueness of the slots and said supportive action enables the anchoring portion or fastening portion to retain its circular shape when compressed radially.

The chippings cut from the wall of the hole drilled in the bone tissue are collected in the cavity and subsequently contribute in strengthening the anchorage in the reformed bone tissue.

The invention claimed is:

1. A fixture shaped and configured to be screwed firmly into bone tissue, said fixture comprising:
a generally cylindrical anchoring portion formed with an insertion end and having an external screw thread, a cavity which opens out at said insertion end, and a plurality of through-penetrating slots extending from said insertion end, wherein each said slot connects the cavity with the outside of said anchoring portion and wherein each said slot is defined by a leading slot wall surface facing each said slot and a trailing slot wall surface facing each said slot, where said leading and trailing wall surfaces relate to the direction of rotation defined by said screw thread when screwing in the fixture, such that said leading slot wall surface is the one that is ahead of each said slot and said trailing slot wall surface is behind each said slot in said direction of rotation, wherein at least the radially outermost part of said trailing slot wall surface defines a cutting edge at an angle $\alpha$ with the radial direction and slopes obliquely forwardly from within and outwardly in said direction of rotation, whereby the cutting edge formed between said at least the radially outermost part of said trailing slot wall surface and the outside of said anchoring portion define an acute angle, and wherein substantially all portions of said trailing slot wall slope obliquely forwardly from within and outwardly in said direction of rotation, and wherein the portion of said anchoring portion that lies between said trailing slot wall and said leading slot wall of the adjacent slot compresses radially when the anchoring portion is screwed into bone tissue to resist distortion of the shape of said anchoring portion.

2. The fixture according to claim 1, wherein the whole of the trailing slot wall surface defines the same angle $\alpha$.

3. The fixture according to claim 2, wherein said leading slot wall surface also slopes obliquely forward from within and outward in said direction of rotation.

4. The fixture according to claim 3, wherein said leading and trailing slot wall surfaces are parallel with one another.

5. The fixture according to claim 4, wherein the angle $\alpha$ is 20°-40° at the radially outer end of the trailing slot wall surface.

6. The fixture according to claim 2, wherein the angle $\alpha$ is 20°-40° at the radially outer end of the trailing slot wall surface.

7. The fixture according to claim 2, wherein the angle $\alpha$ is 27°-33° at the radially outer end of the trailing slot wall surface.

8. The fixture according to claim 2, wherein the slots are 3-10 in number.

9. The fixture according to claim 2, wherein the slots are 5-7 in number.

10. The fixture according to claim 2, wherein the cavity is circular in cross-section and widens conically in a direction toward said insertion end.

11. The fixture according to claim 2, wherein the slot width at the radially outer end of said slot corresponds to 15-35% of the peripheral distance between the two slots on the outside of the fixture.

12. The fixture according to claim 3, wherein the angle $\alpha$ is 20°-40° at the radially outer end of the trailing slot wall surface.

13. The fixture according to claim 3, wherein the slots are 5-7 in number.

14. The fixture according to claim 3, wherein the cavity is circular in cross-section and widens conically in a direction toward said insertion end.

15. The fixture according to claim 3, wherein the slot width at the radially outer end of said slot corresponds to 15-35% of the peripheral distance between the two slots on the outside of the fixture.

16. The fixture according to claim 1, wherein the angle $\alpha$ is 27°-33° at the radially outer end of the trailing slot wall surface.

17. The fixture according to claim 1, wherein the slots are 3-10 in number.

18. The fixture according to claim 1, wherein the slots are 5-7 in number.

19. The fixture according to claim 1, wherein the cavity is circular in cross-section and widens conically in a direction toward said insertion end.

20. The fixture according to claim 19, wherein the slot width at the radially outer end of said slot corresponds to 15-35% of the peripheral distance between the two slots on the outside of the fixture.

21. The fixture according to claim 1, wherein the slot width at the radially outer end of said slot corresponds to 15-35% of the peripheral distance between the two slots on the outside of the fixture.

22. The fixture according to claim 1, wherein the fixture is made of titanium.

23. The fixture according to claim 1, wherein the angle $\alpha$ is 20°-40° at the radially outer end of the trailing slot wall surface.

24. A fixture shaped and configured to be screwed longitudinally into hollow or tubular bone tissue, said fixture comprising:
a generally cylindrical anchoring portion formed with an insertion end and having an external screw thread, a cavity which opens out at said insertion end, and a plurality of through-penetrating slots extending from said insertion end, wherein each said slot connects the cavity with the outside of said anchoring portion and wherein each said slot is defined by a leading slot wall surface facing each said slot and a trailing slot wall surface facing each said slot, where said leading and trailing wall surfaces relate to the direction of rotation defined by said screw thread when screwing in the fixture, such that said leading slot wall surface is the one that is ahead of each said slot and said trailing slot wall surface is behind each said slot in said direction of rotation, wherein at least the radially outermost part of said trailing slot wall surface defines a cutting edge at an angle $\alpha$ with the radial direction and slopes obliquely forwardly from within and outwardly in said direction of rotation, whereby the cutting edge formed between said at least the radially outermost part of said trailing slot wall surface and the outside of said anchoring portion define an acute angle, and wherein substantially all portions of said trailing slot wall slope obliquely forwardly from within and outwardly in said direction of rotation, and wherein the portion of said anchoring portion that lies between said trailing slot wall and said leading slot wall of the adjacent slot compresses radially when the anchoring portion is screwed into bone tissue to resist distortion of the shape of said anchoring portion.

* * * * *